United States Patent [19]
Fritsch et al.

US005606050A

[11] Patent Number: 5,606,050
[45] Date of Patent: Feb. 25, 1997

[54] METHOD FOR SOLUBILIZING POLY(1-3)GLUCOPYRANOSE

[75] Inventors: Marie C. Fritsch, Paris; Pierre Peyramaure, Suresnes, both of France

[73] Assignee: Institut de Recherches et D'Innovations Scientifiques (I.R.I.S.), Paris, France

[21] Appl. No.: 407,022

[22] PCT Filed: Jul. 27, 1994

[86] PCT No.: PCT/FR94/00940

§ 371 Date: May 9, 1995

§ 102(e) Date: May 9, 1995

[87] PCT Pub. No.: WO95/04107

PCT Pub. Date: Feb. 9, 1995

[30] Foreign Application Priority Data

Jul. 28, 1993 [FR] France ................................ 93 09389

[51] Int. Cl.$^6$ .............................. C08L 5/00; C08B 37/00; C08J 3/09

[52] U.S. Cl. .................... 536/123.1; 536/123.12; 536/123.13; 424/63; 424/69; 424/70.1; 424/78.02; 514/777; 514/844; 514/845; 514/846; 514/847; 514/848

[58] Field of Search ........................ 536/123.1, 123.12, 536/123.13; 424/69, 70.1, 63, 78.02; 514/777, 844, 845, 846, 847, 848

[56] References Cited

U.S. PATENT DOCUMENTS 3,659,025  4/1972  Halleck .................................. 514/777

*Primary Examiner*—Nathan M. Nutter
*Attorney, Agent, or Firm*—Browdy and Neimark

[57] ABSTRACT

The method for solubilizing poly(1–3)glucopyranose consists in mixing it with a composition comprising sorbitol, in a proportion exceeding 80%, preferably 90%, and an additive comprising water and/or glycerin and/or propylene glycol.

9 Claims, No Drawings

METHOD FOR SOLUBILIZING POLY(1-3)GLUCOPYRANOSE

BACKGROUND OF THE INVENTION

1. Field of the Invention

This invention relates to a method for solubilizing poly(1–3)glucopyranose in a medium compatible with a subsequent incorporation into a cosmetic preparation.

2. Description of the Prior Art

Its object is also a cosmetic composition using poly(1–3)glucopyranose solubilized by said method.

It should be recalled that poly(1–3)glucopyranose is a long-chain polysaccharide extracted e.g. from yeast cell walls, and comes in the form of a beige-colored, odourless powder that is insoluble in water, and is marketed by Immudyne Inc. under the "Nayad" trademark. It is classified in the chemical category of homogeneous polyhexoses, a category which includes, inter alia:

the dextrans which are soluble in an aqueous medium, forming colloidal solutions of viscosity varying as a function of molecular weight, amylum which is not soluble in water but which, when brought to 100° C., forms well-known starch, cellulose which is insoluble in water and in the usual solvents.

Studies conducted to date on the solubilization of polysaccharides other than starches reveal that:

The neutral polysaccharides such as dextran, levan, scleroglucane can be directly solubilized by DMSO $((CH_3)_2SO)$. However, this solvent has the drawback of being incompatible with incorporation into a cosmetic product.

The combined action of 4-methylmorpholine-n-oxide and DMSO enables an overall solubilizing of polysaccharides other than starch. However, in this case, a 120° C. heating stage is required to extract the products. Because of this, the integrity of the poly(1–3)glucopyranose cannot be guaranteed and, furthermore, this method is subject to the same incompatibility problems as above.

The utilisation of sodium hydroxide, NaOH, which, however, produces variations in the viscosity of the scleroglucane, has not enabled significant results to be obtained in the case of poly(1–3)glucopyranose. These observations tend to confirm that poly(1–3) glucopyranose is not really a scleroglucane.

These studies have not enabled the determination of a solubilizing method applicable to poly(1–3)glucopyranose and compatible with cosmetic applications.

The filing party has therefore conducted tests using agents such as polyalcohols to wet the powder and facilitate dispersion thereof in water.

Accordingly, a series of experiments have been conducted with a view to assessing the solubility of glucopyranose in a range of sorbitol/distilled water mixtures, at temperatures ranging from +25° C. to +100° C., in order to select the solvent enabling optimal dissolution of the product at the lowest possible temperature.

In the course of these experiments, the solutions were subjected to rising temperatures (by increments of 10° C. up to 100° C.) for periods of one to two hours, with a rest time of approximately half an hour between each temperature stage. Once the appearance of the solutions so permitted (homogeneity and absence of aggregates in suspension), a spectrophotometric reading was taken at 600 nm in order to assess the degree of opacity.

All solutions were maintained at room temperature for 48 hours. Upon expiry of this period, appearance and absorbance at 600 nm were recorded.

The results obtained have been set forth in Table I hereafter which only takes into account temperatures from 50° C. up (absorbance could not be measured below this temperature as the majority of solutions were not homogeneous).

They show that irrespective of the composition of the solvent mixture, a heating stage is indispensable for dispersion of the active principle, the minimum temperature being 50° C. Moreover, as the proportion of sorbitol increases, dispersion becomes easier at low temperature and the opacity of the mixture decreases. Furthermore, the threshold of temperature required to obtain an apparent dissolution of the active principle decreases as the proportion of sorbitol is increased.

TABLE I

| Composition of the solvent mixture | | TEMPERATURE | | | | | |
|---|---|---|---|---|---|---|---|
| Water | Sorbitol | +50° C. | | +60° C. | | +80° C. | +100° C. |
| (V) | (V) | 1 h | 2 h | 1 h | 2 h | 1 h | 1 h |
| 100 | 0 | 1.368 | 1.419 | 1.387 | 1.361 | 1.299 | 1.369 |
| 90 | 10 | 1.347 | 1.351 | 1.335 | 1.310 | 1.293 | 1.292 |
| 80 | 20 | 1.259 | 1,255 | 1,240 | 1.246 | 1.234 | 1.206 |
| 70 | 30 | 1.150 | 1.142 | 1.110 | 1.096 | 1.080 | 1.098 |
| 60 | 40 | 1.035 | 1.029 | 1.002 | 0.997 | 0.975 | 0.996 |
| 50 | 50 | 0.912 | 0.888 | 0.849 | 0.822 | 0.817 | 0.838 |
| 40 | 60 | 0.774 | 0.774 | 0.736 | 0.730 | 0.704 | 0.720 |
| 30 | 70 | 0.784 | 0.716 | 0.668 | 0.653 | 0.609 | 0.633 |
| 20 | 80 | 0.637 | 0.594 | 0.562 | 0.551 | 0.512 | 0.535 |
| 10 | 90 | 0.504 | 0.492 | 0.482 | 0.467 | 0.438 | 0.449 |
| 0 | 100 | 0.477 | 0.433 | 0.418 | 0.420 | 0.377 | 0.394 |

From 80% sorbitol upwards, up to 48 hours at rest, the solution remains stable at room temperature and then forms a deposit which can disappear when the solution is stirred. It is unstable from 0° C. to 50° C.

It is obvious that even if these results are encouraging and constitute real progress, in particular for percentages of sorbitol of the order of 90%, the instabilities observed after 48 hours and at 0° C. and 50° C. continue to be a considerable inconvenience.

OBJECT OF THE INVENTION

The main object of this invention is to remedy the preceding disadvantages.

SUMMARY OF THE INVENTION

Accordingly, there is provided a method for solubilizing β1-3glucopyranose which consists in mixing it with a composition comprising sorbitol in a proportion exceeding 80%, preferably of 90%, and an additive comprising two compounds selected from among the following three compounds: water, glycerin and propylene glycol.

When the additive comprises water, its composition will preferably be:

water: 2.0% to 4.5% glycerin or propylene glycol: 7.4% to 4.9%

If the additive does not comprise water, its composition will preferably be:

glycerin: 2.4% to 7.4% propylene glycol: 7.0% to 2.0%

(solution producing the best results in terms of stability)

Advantageously, the additive will represent 9.4% of the mixture.

Tests conducted on the mixture comprising β1-3glucopyranose in a proportion of 0.1%, and various compositions comprising sorbitol, phenonip and demineralized water and/ or propylene glycol, have enabled the following Table II of results to be drawn up:

The results listed in columns 4 and 5 were obtained with a mixture of propylene glycol and glycerin replacing part of the distilled water. They reveal:

- a better improvement of the appearance (almost transparent),
- satisfactory stability at room temperature and at 0° C.,
- a very slight improvement in stability at 50° C.

Columns 6 to 9 refer to compositions in which water has been completely suppressed and replaced with propylene glycol or glycerin (columns 6 and 7), and by a combination of propylene glycol and glycerin in predetermined proportions (columns 8 and 9).

TABLE II

| | Composition No | | | | | | | | |
|---|---|---|---|---|---|---|---|---|---|
| | 1 % w/w | 2 % w/w | 3 % w/w | 4 % w/w | 5 % w/w | 6 % w/w | 7 % w/w | 8 % w/w | 9 % w/w |
| Sorbitol | 90.00 | 85.00 | 85.00 | 90.00 | 90.00 | 90.00 | 90.00 | 90.00 | 90.00 |
| Glucopyranose | 0.1 | 0.1 | 0.01 | 0.10 | 0.10 | 0.10 | 0.10 | 0,10 | 0.10 |
| Demineralized water | 9.40 | 9.40 | 9.40 | 4.40 | 4.40 | | | | |
| Propylene glycol | | 5.00 | | 5.00 | | 9.40 | | 6,90 | 2.20 |
| Glycerin | | | 5.00 | | 5.00 | | 9.40 | 2.50 | 7.20 |
| Phenonip | 0.50 | 0.50 | 0.50 | 0.50 | 0.50 | 0.50 | 0.50 | 0.50 | 0.50 |
| appearance | cloudy | opalescent | opalescent | almost transparent | almost transparent | opalescent | cloudy | transparent | transparent |
| Stability at 50° C. | | | | | | | | | |
| 1 week | deposit | slight deposit | slight deposit | slight deposit | very sl. deposit | slight deposit | —(*) | — | — |
| 2 weeks | deposit | deposit | deposit | deposit | deposit | slight deposit | — | — | — |
| 3 weeks | deposit | deposit | deposit | deposit | deposit | deposit | slight deposit | — | — |
| 4 weeks | deposit | deposit | deposit | deposit | deposit | deposit | deposit | — | — |
| Stability at 0° C. | | | | | | | | | |
| 1 week | slight deposit | — | — | — | — | — | — | — | — |
| 2 weeks | deposit | — | — | — | — | — | — | — | — |
| 3 weeks | deposit | deposit | deposit | — | — | — | — | — | — |
| 4 weeks | deposit | deposit | deposit | — | — | — | — | — | — |
| Stability at room temperature | | | | | | | | | |
| 1 week | slight deposit | — | — | — | — | — | — | — | — |
| 2 weeks | deposit | slight deposit | slight deposit | — | — | — | — | — | — |
| 3 weeks | deposit | deposit | deposit | — | — | — | — | — | — |
| 4 weeks | deposit | deposit | deposit | — | — | — | — | — | — |

(*)— = nothing to report

In this table, column 1 refers to a solubilization test using sorbitol (90%), demineralized water (9.4%) and a preservative such as phenonip (0.5%). This test merely confirms the results previously obtained, i.e.

- improved dispersion,
- improved appearance (pseudosolution less cloudy),
- stability for 48 hours at room temperature followed by the formation of a deposit that can temporarily disappear with stirring of the solution,
- instability from 50° C. to 0° C.

Columns 2 and 3 correspond to tests in which part of the sorbitol has been replaced by propylene glycol and glycerin. The results observed subsequent to the test were as follows:

- improved appearance (opalescent solution),
- improvement in stability at room temperature and at 0° C. (this stability remains nonetheless insufficient),
- no improvement in stability at 50° C.

The tests illustrated in columns 6 and 7 produce the following results:

- no improvement in the appearance and a reversal to cloudy (glycerin) or opalescent (propylene glycol) solutions,
- satisfactory stability at room temperature and at 0° C.,
- a slight improvement in stability at 50° C.

Conversely, columns 8 and 9 reveal highly satisfactory results, with:

- improved appearance, transparent solutions,
- satisfactory stability at room temperature and at 50° C.

By way of these results, it becomes possible to obtain a solubilization of β1-3glucopyranose by means of constituents that are fully compatible with applications in the field of cosmetics.

We claim:

1. A method for solubilizing a non-water soluble powder of poly-(1–3)glucopyranose, comprising mixing said poly- (1–3)glucopyranose with a solvent mixture comprising (1) more than 80% sorbitol, and (2) an additive comprising two compounds selected from among the following three compounds: water, glycerin and propylene glycol.

2. The method as claimed in claim 1, wherein the proportion of glucopyranose is of the order of 0.1%.

3. The method as claimed in claim 1, wherein the additive comprises water: 2.0% to 4.5% glycerin or propylene glycol: 7.4% to 4.9%.

4. The method as claimed in claim 1, wherein the additive does not comprises substantially no water, and glycerin: 2.4% to 7.4%.

propylene glycol: 7.0% to 2.0%.

5. The method as claimed in claim 1, wherein additive represents 9.4% of the solvent mixture.

6. The method as claimed in claim 1, wherein the additive further comprises a preservative in a proportion of 0.5%.

7. The method as claimed in claim 6, wherein said preservative is phenonip.

8. A method according to claim 1, wherein sorbitol is in a proportion exceeding 90%.

9. A cosmetic composition comprising a non water soluble powder of poly(1–3)glucopyranose and a solvent mixture comprising sorbitol in a proportion exceeding 80%, and an additive comprising two compounds selected from among water, glycerin and a propylene glycol.

\* \* \* \* \*